United States Patent
Akle et al.

(10) Patent No.: US 11,554,166 B2
(45) Date of Patent: *Jan. 17, 2023

(54) IMMUNOGENIC TREATMENT OF CANCER

(71) Applicant: IMMODULON THERAPEUTICS LIMITED, London (GB)

(72) Inventors: Charles Akle, Uxbridge (GB); Satvinder Mudan, London (GB); John Grange, London (GB)

(73) Assignee: IMMODULON THERAPEUTICS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/916,194

(22) Filed: Jun. 30, 2020

(65) Prior Publication Data

US 2020/0338181 A1 Oct. 29, 2020

Related U.S. Application Data

(63) Continuation of application No. 16/225,028, filed on Dec. 19, 2018, now Pat. No. 11,318,193, which is a continuation of application No. 14/361,992, filed as application No. PCT/GB2012/052992 on Dec. 3, 2012, now abandoned.

(30) Foreign Application Priority Data

Dec. 2, 2011 (GB) .................................. 1120779

(51) Int. Cl.
| | |
|---|---|
| *A61K 39/04* | (2006.01) |
| *A61K 39/00* | (2006.01) |
| *A61K 35/74* | (2015.01) |
| *A61K 45/06* | (2006.01) |
| *A61N 5/10* | (2006.01) |

(52) U.S. Cl.
CPC .............. *A61K 39/04* (2013.01); *A61K 35/74* (2013.01); *A61K 45/06* (2013.01); *A61N 5/1001* (2013.01); *A61K 2039/521* (2013.01)

(58) Field of Classification Search
None
See application file for complete search history.

(56) References Cited

U.S. PATENT DOCUMENTS

| | | | |
|---|---|---|---|
| 5,207,223 A | 5/1993 | Adler | |
| 5,458,125 A | 10/1995 | Schewikard | |
| 5,599,545 A | 2/1997 | Stanford et al. | |
| 8,367,075 B2 | 2/2013 | Nandi et al. | |
| 8,617,520 B2 | 12/2013 | Akle et al. | |
| 10,610,577 B2 | 4/2020 | Akle et al. | |
| 10,610,578 B2 | 4/2020 | Akle et al. | |
| 11,318,193 B2* | 5/2022 | Akle ..................... | A61P 35/02 |
| 2005/0187207 A1 | 8/2005 | Curry et al. | |
| 2006/0110383 A1 | 5/2006 | Honjo et al. | |
| 2008/0318252 A1 | 12/2008 | Kachlany | |
| 2009/0304749 A1 | 12/2009 | Stanford et al. | |
| 2013/0004456 A1 | 1/2013 | Weinschenk et al. | |
| 2013/0209517 A1 | 8/2013 | Akle et al. | |
| 2014/0018606 A1 | 1/2014 | Raman et al. | |
| 2015/0284416 A1 | 10/2015 | Zhao | |
| 2017/0007693 A1 | 1/2017 | Weiner et al. | |
| 2018/0185479 A1 | 7/2018 | Akle et al. | |
| 2020/0215175 A1 | 7/2020 | Akle et al. | |
| 2020/0215176 A1 | 7/2020 | Akle et al. | |

FOREIGN PATENT DOCUMENTS

| | | |
|---|---|---|
| EP | 2620159 | 7/2013 |
| WO | WO 00/64476 | 11/2000 |
| WO | WO 03/049751 | 6/2003 |
| WO | WO 2004/006837 | 1/2004 |
| WO | WO 2007/050405 | 5/2007 |
| WO | WO 2007/071978 | 6/2007 |
| WO | WO 2007/112316 | 10/2007 |
| WO | WO 2008/110491 | 9/2008 |
| WO | WO 2008/156712 | 12/2008 |
| WO | WO 2012/177624 | 12/2012 |
| WO | WO 2013/114367 | 8/2013 |
| WO | WO 2014/181121 | 11/2014 |
| WO | WO 2015/092382 | 6/2015 |
| WO | WO 2016/207646 | 12/2016 |
| WO | WO 2020/002905 | 1/2020 |

OTHER PUBLICATIONS

Gameiro et al. PLOS ONE 8: e70417, pp. 1-13, 2013.*
Study No. IMM-101-007 (Completed), Jun. 22, 2012.*
A Study of IMM-101 in Combination With Radiation Induced Tumour Necrosis in Colorectal Cancer. NCT01539824, pp. 1-9, Feb. 28, 2012.*
Golden and Formenti. Int. J. Radiation Oncol. Biol. Phys. 91: 252-254, Feb. 2015.*
Sroufe et al. Transl Lung Cancer Res. 4: 438-447, Aug. 2015.*
Rwigema et al. Presented in the 51st Annual Meeting of the American Society for Radiation Oncology, Chicago, IL, Nov. 1-4, #2190, 2009; I. J. Radiation. Oncol. Biol. Phys. 75: S266-S267, #2190, Sep. 2009.*
Polistina et al. Radiother. Oncol. 99: 120-123, available online May 27, 2011.*

(Continued)

*Primary Examiner* — S. Devi
(74) *Attorney, Agent, or Firm* — Saliwanchik, Lloyd & Eisenschenk

(57) ABSTRACT

The present invention provides an immunomodulator for use in the treatment and/or control of a neoplastic disease in a patient intended to undergo immunogenic cell death therapy simultaneously, separately or sequentially with administration of the immunomodulator. The therapy can be selected from microwave irradiation, targeted radiotherapy, embolisation, cryotherapy, ultrasound, high intensity focused ultrasound, cyberknife, hyperthermia, radiofrequency ablation, cryoablation, electrotome heating, hot water injection, alcohol injection, embolization, radiation exposure, photodynamic therapy, laser beam irradiation, and combinations thereof.

14 Claims, 1 Drawing Sheet

(56) References Cited

OTHER PUBLICATIONS

Costa Neves, M. et al. "Extended Survival after Complete Pathological Response in Metastatic Pancreatic Ductal Adenocarcinoma Following Induction Chemotherapy, Chemoradiotherapy, and a Novel Immunotherapy Agent, IMM-101", Cureus, Dec. 26, 2015, 7(12):e435.
Study protocol information for Phase II Clinical Trial NCT01303172 from ClinicalTrials.Gov, downloaded Jun. 15, 2020.
International Search Report and Written Opinion for PCT/GB2014/053717 (WO 2015/092382) dated Mar. 10, 2015.
International Search Report and Written Opinion for PCT/GB2016/051893 (WO 2016/207646) dated Sep. 15, 2016.
Pending claims in U.S. Appl. No. 16/819,927, filed Mar. 24, 2020, pp. 1-3.
Pending claims in U.S. Appl. No. 16/820,058, filed Mar. 24, 2020, pp. 1-3.
Pending claims in U.S. Appl. No. 16/820,132, filed Mar. 24, 2020, pp. 1-3.
Pending claims in U.S. Appl. No. 16/916,194, filed Jun. 30, 2020, pp. 1.
Weledji et al. Oncol. Rev. 10: 294, pp. 28-37, 2016.
Richards S. Fred Hutch News Service, pp. 1-5, May 10, 2016.
Fowler et al. J. Immunother. Cancer 2: suppl 3: P54, 2014.
Finkelstein et al. Clin. Dev. Immunol. vol. 2011, pp. 1-7, 2011.
Final Office Action in U.S. Appl. No. 14/361,992 dated Aug. 16, 2017, 16 pages.
Final Office Action in U.S. Appl. No. 14/361,992 dated Jul. 5, 2016, 10 pages.
Non-Final Office Action in U.S. Appl. No. 14/361,992 dated Apr. 3, 2017, 8 pages.
Non-Final Office Action in U.S. Appl. No. 14/361,992 dated Jun. 28, 2018, 12 pages.
Non-Final Office Action in U.S. Appl. No. 14/361,992 dated Nov. 6, 2015, 8 pages.
PCT International Search Report in PCT/GB2012/052992, dated Mar. 1, 2013, 5 pages.
Ayaru, Lakshmana, et al., "Unmasking of a-Fetoprotein-Specific CD4+ T Cell Responses in Hepatocellular Carcinoma Patients Undergoing Embolization", The Journal of Immunology, vol. 178, 2007, 1914-1922.
Balkwill, Fran, et al., "Inflammation and cancer: back to Virchow?", The Lancet: Review vol. 357, Feb. 17, 2001, 539-545.
Castano, Ana P, et al., "Photodynamic therapy and anti-tumor immunity", Nature Reviews: Cancer vol. 6, Jul. 2006, 535-545.
Dalgleish, Angus George, "A multicenter randomized, open-label, proof-of-concept, phase II trial comparing gemcitabine with and without IMM-101 in advanced pancreatic cancer", J. Oncology Suppl. 336, 2015, 1 pg.
Den Brok, M.H.M.G.M., et al., "Efficient loading of dentritic cells following cryo and radiofrequency ablation in combination with immune modulation induces anti-tumor immunity", British Journal of Cancer vol. 95, 2006, 896-905.
Den Brok, Martijn H.M.G.M., et al., "Synergy between In situ Cryoablation and TLR9 Stimulation Results in a Highly Effective In vivo Dentritic Cell Vaccine", Cancer Res. vol. 66 No. 14, Jul. 15, 2006, 7285-7292.
Dunn, Gavin P, et al., "The Three Es of Cancer Immunoediting", Annu. Rev. Immunol. vol. 22, 2004, 329-360.
Dvorak, Harold F, "Tumors: Wounds That Do Not Heal—Similarities between Tumor Stroma Generation and Wound Healing", The New England Journal of Medicine, vol. 315, No. 26, Dec. 25, 1986, 1650-1659.
Finkelstein, Steven Eric, et al., "The Confluence of Stereotactic Ablative Radiotherapy and Tumor Immunology", Clinical and Developmental Immunology, vol. 2011, Article ID: 439752, doi: 10/11552011/439752, 2011, 1-7.
Hrouda, D., et al., "Immunotherapy of advanced prostate cancer: a phase I/II trial using *Mycobacterium vaccae* (SRL172)", British Journal of Urology 82, 1998, 568-573.
Jerome, Keith R, et al., "The Danger Within", The New England Journal of Medicine, vol. 350, No. 4, Jan. 22, 2004, 411-412.
Korbelik, Mladen, et al., "Enhancement of tumour response to photodynamic therapy by adjuvant *Mycobacterium* cell-wall treatment", Journal of Photochemistry and Photobiology B: Biology, vol. 44, 1998, 151-158.
Korbelik, Mladen, et al., "Interaction Between Photodynamic Therapy and BCG Immunotherapy Responsible for the Reduced Recurrence of Treated Mouse Tumors", Photochemistry and Photobiology, vol. 73, No. 4, pp. 403-409 (2001).
Kumar, Prabjr, et al., "Role of *Mycobacterium* was Adjuvant Treatment of Lung Cancer (Non-small Cell Lung Cancer)", J. Indian. Med. Assoc. vol. 101, No. 2, Feb. 2003, 2 pages.
Ma, Xiaopeng, et al., "Combination sonodynamic therapy with immunoadjuvant may be a promising new modality for cancer treatment", Medical Hypotheses, vol. 72, 2009, 418-420.
Morse, Michael A, et al., "An Odd But Synergistic Couple: Immunotherapy Combined With Radiotherapy", Cancer Network: Home of the Journal Oncology, Aug. 1, 2008, 3 pages.
Napoletano, Chiara, et al., "RFA strongly modulates the immune syste and anti-tumor immune responses in metastatic liver patients", International Journal of Oncology, vol. 32, 2008, 481-490.
O'Brien, Mer, et al., "A randomized phase II strudy of SRL172 (Nycobacterium vaccae) combined with chemotherapy in patients with advanced inoperable non-small-cell lung cancer and mesothelioma", British Journal of Cancer vol. 83 No. 7, 2000, 853-857.
Oka, Hideki, et al., "Z-100, an Immunomodulatory Arabinomannan Extracted from *Mycobacterium tuberculosis* Strain Aoyama B, Augments Anti-tumor Actvities of X-Ray Irradiation against B16 Melanoma in Association with the Improvement of Type 1T Cell Responses", Biol. Pharm. Bull. vol. 27 No. 1, 2004, 82-88.
Schwartsburd, P.M., "Chronic inflammation as inductor of procancer microenvironment: Pathogenesis of dysregulated feedback control", Cancer and Metastasis Reviews, vol. 22, 2003, 95-102.
Shankar, Bhavani, et al., "Modification of immune response by low dose ionizing radiation: role of apoptosis", Immunology Letters 68, 1999, 237-245.
Slaviero, Kellie A, et al., "Inflammatory response: an unrecognised source of variability in the parmacokinetics and pharmacodynamics of cancer chemotherapy", The Lancet: Oncology, vol. 4, Apr. 2003, 224-232.
Stebbing, J., et al., "An intra-patient placebo-controlled phase I trial to evaluate the safety and tolerability of intradermal IMM-101 in melanoma", Annals of Oncology, doi: 10.1093/annonc/mdr363, Sep. 19, 2011, 1-6.
Tang, Xiaolin, et al., "Design of Freeze-Drying Processes for Pharmaceuticals: Practical Advice", Pharmaceutical Research, vol. 21, No. 2, Feb. 2004, 10 pgs.
Tesniere, A, et al., "Molecular characteristics of immunogenic cancer cell death", Cell Death and Differentiation vol. 15, 2008, 3-12.
Vakkila, Jukka, et al., "Inflammation and necrosis promote tumor growth", Nature Reviews: Immunology vol. 4, Aug. 2004,6410648.
Vogl, Thomas Josef, et al., "Activation of tumor-specific T lymphocytes after laser-induced termotherapy in patients with colorectal liver metastases", Cancer Immunol. Immunother. vol. 58, 2009, 1557-1563.
Williams, Lynda, "Medical Research News, pp. 1-2, Feb. 19, 2013".
Yuk, Jae-Min, et al., "Bacillus calmette-guerin cell wall cytoskeleton enhances colon cancer radiosensitivity through autophagy", Autophagy, vol. 6, Issue 1, Jan. 1, 2010, 15 pgs.
Zeh, III, Herbert J., et al., "Addicted to Death—Invasive Cancer and the Immune Response to Unscheduled Cell Death", J. Immunother., vol. 28, No. 1, Jan./Feb. 2005, pp. 1-9.
Zerbini, Alessandro, et al., "Radiofrequency Thermal Ablation of Hepatocellular Carcinoma Liver Nodules Can Activate and Enhance Tumor-Specific T-Cell Responses", Cancer Research vol. 66 No. 2, Jan. 15, 2006, 1139-1146.

(56) References Cited

OTHER PUBLICATIONS

Zitvogel, Laurence, et al., "Immune Response Against Dying Tumor Cells", Advances in Immunology, vol. 84, 2004, 131-179.
Zitvogel, Laurence, et al., "The anticancer immune response: indispensable for therapeutic success?", The Journal of Clinical Investigation vol. 118 No. 6, Jun. 2008, 1991-2001.
Ai, M. et al. "Immune checkpoint combinations from mouse to man" Cancer Immunol Immunother, 2015, pp. 885-892, vol. 64.
Cananzi, F.C.M. et al. "Long-term survival and outcome of patients originally given Mycobacterium vaccae for metastatic malignant melanoma" Human Vaccines & Immunotherapeutics, 2013, 9(11):2427-2433.
Center for Drug Evaluation and Research, "BLA Multidisciplinary Review and Evaluation: BLA 761049 Bavencio (Avelumab)," Reference ID: 4073902, Feb. 2016, 194 pages.
Center for Drug Evaluation and Research, "Imfinzi CDER Pharmacology and Biopharmaceutics Review," Reference ID 4065384, Clinical Pharmacology and Biopharmaceutics Review(s), Mar. 2017, 49 pages.
Center for Drug Evaluation and Research, "Yervoy CDER Pharmacology Review," Reference ID 125377, Clinical Pharmacology and Biopharmaceutics Review(s), Mar. 2011, 131 pages.
Crooks, J. et al., "The effects of combination treatment of IMM-101, a heat-killed whole cell preparation of Mycobacterium obuense (NCTC 13365) with checkpoint inhibitors in pre-clinical models," 31st Annual Meeting, Society for Immunotherapy of Cancer, Poster No. 240, p. 1, (2016).
Crooks, J. et al., Abstract of "The effects of combination treatment of IMM-101, a heat-killed whole cell preparation of Mycobacterium obuense (NCTC 13365) with checkpoint inhibitors in pre-clinical models," J. for ImmunoTherapy of Cancer, 4 (Suppl 1): P233 (2016).
Dalgleish, A. et al., Abstract of "Five year survival in patients with metastatic melanoma receiving IMM-101," Annals of Oncology 26(Suppl 8): 5-14, pp. 1-2, (2015).
Dalgleish, A. et al., "Does IMM-101 prime for increased clinical responses to checkpoint inhibitors in metastatic melanoma and pancreatic cancer?" 31st Annual Meeting, Society for Immunotherapy of Cancer, Poster No. 204, p. 1, (2016).
Dalgleish, A. et al., "Enhanced effect of checkpoint inhibitors when given after or together with IMM-101: significant responses in four advanced melanoma patients with No. additional major toxicity," J. Transl. Med. 16:227, pp. 1-7, (2018).
Dalgleish, A. et al., "Randomised, open-label, phase II study of gemcitabine with and without IMM-101 for advanced pancreatic cancer," Brit. J. of Cancer 115:789-796 (2016).
Declaration of Angus G. Dalgleish, M.D., under 37 CFR §1.132, dated Dec. 19, 2018, submitted in U.S. Appl. No. 15/104,890.
Elia, A. et al. "Treatmentwith IMM-101 induces protective CD8+ T cell responses in clinically relevant models of pancreatic cancer", Journal for ImmunoTherapy of Cancer, 1 (Suppl 1): p. 215 (2013).
Food and Drug Administration, "Highlights of Prescribing Information: BAVENCIO," Medical Guide, Reference ID 4095102, May 2017, 25 pages.
Food and Drug Administration, "Highlights of Prescribing Information: IMFINZI," Medical Guide, Reference ID 4223035, Feb. 2018, 27 pages.
Food and Drug Administration, "Highlights of Prescribing Information: KEYTRUDA," Medication Guide, Reference ID 4449844, Jun. 2019, 80 pages.
Food and Drug Administration, "Highlights of Prescribing Information: OPDIVO," Medication Guide, Reference ID 4427750, May 2019, 78 pages.
Food and Drug Administration, "Highlights of Prescribing Information: TECENTRIQ," Medication Guide, Reference ID 4000525, Oct. 2016, 23 pages.
Food and Drug Administration, "Highlights of Prescribing Information: YERVOY," Medication Guide, Reference ID 4430687, May 2019, 52 pages.
Fowler, D. W. et al. "Mycobacteria activate gamma-delta T-cell anti-tumour responses via cytokines from type 1 myeloid dendritic cells: a mechanism of action for cancer immunotherapy", Cancer Immunol Immunotherapy, 61:535-547 (2012).
Houot, R. and Levy, R. "T-cell modulation combined with intratumoral CpG cures lymphoma in a mouse model without the need for chemotherapy" Blood, 2009, 113:3546-3552.
Hrouda, D. et al., "Allogeneic whole-tumour cell vaccination in the rat model of prostate cancer," BJU International, vol. 86, No. 6, Oct. 2000, pp. 742-748. ISSN: 1464-4096.
International Preliminary Report on Patentability, PCT Application No. PCT/GB2012/052992, dated Jan. 24, 2014, 7 pages.
International Search Report and Written Opinion for corresponding International Patent Application No. PCT/GB2016/051893, dated Dec. 29, 2016, 12 pages.
International Search Report and Written Opinion for corresponding International Patent Application No. PCT/GB2016/051893, dated Jan. 29, 2016, 11 pages.
Maverakis, E. et al. "Metastatic Melanoma—A Review of Current and Future Treatment Options" Acta Derm Venereol., 2015, 95:516-524.
Pending claims in U.S. Appl. No. 16/916,194, filed Jul. 1, 2020, pp. 1.
Powles, "Inhibition of PD-L1 by MPDL3280A and clinical activity in pts with metastatic urothelial bladder cancer (UBC)" J. Clin. Oncology, 2014, 32(15_Suppl):5011, abstract.
Ricks, T.K., "Tecentriq CDER Pharmacology Review," Center for Drug Evaluation and Research, Reference ID 3920269, BLA # 761034, Apr. 2016, 58 pages.
Sur, P.K. et al., "Role of Mycobacterium was adjuvant treatment of lung cancer (non-small cell lung cancer)," Journal of the Indian Medical Association, Indian Medical Association, Calcutta, IN, vol. 101, No. 2, Feb. 2003, p. 118,120, XP009115704, ISSN:0019-5847.
United States Office Action, U.S. Appl. No. 15/104,890, dated Apr. 24, 2018, 12 pages.
United States Office Action, U.S. Appl. No. 15/104,890, dated Aug. 30, 2017, 7 pages.
United States Office Action, U.S. Appl. No. 15/104,890, dated Feb. 15, 2019, 15 pages.
United States Office Action, U.S. Appl. No. 15/104,890, dated Jan. 9, 2017, 22 pages.
United States Office Action, U.S. Appl. No. 15/104,890, dated May 22, 2017, 10 pages.
Weis, S.L. et al., "Opdivo CDER Pharmacology Review," Center for Drug Evaluation and Research, Reference ID: 3667795, Dec. 2014, 99 pages.
Weis, S.L., "Keytruda CDER Pharmacology Review," Center for Drug Evaluation and Research, Reference ID: 3601748, Aug. 2014, 97 pages.
Wolchok, J.D. et al. "Guidelines for the Evaluation of Immune Therapy Activity in Solid Tumors: Immune-Related Response Criteria" Clin. Cancer Res., 2009, 15(23):7412-7420.
Wong, K.P. et al., "Effects of Administration Route, Dietary Condition, and Blood Glucose Level on Kinetics and Uptake of 18F-FDG in Mice," The Journal of Nuclear Medicine, May 2011, vol. 52, No. 5, 9 pages.
Zahalka, E., "Imfinzi CDER Pharmacology Review," Center for Drug Evaluation and Research, Reference ID 4070413, BLA#761069, Mar. 2017, 70 pages.
Zamarin, D. et al. "Localized oncolytic virotherapy overcomes systemic tumor resistance to immune checkpoint blockade immunotherapy" Sci. Transl. Med., 2014, 6(226):226ra32.
"Checkpoint inhibitor" definition on Wikipedia, "https://en.wikipedia.org/w/index.php?title=Checkpoint_inhibitor&oldid=990545057", retrieved Dec. 1, 2020.
Pardoll, D. "The blockade of immune checkpoints in cancer immunotherapy" Nat. Rev. Cancer, 2016, 12(4):252-264.
Gaya, A. "A phase II, single arm, investigative study of IMM-101 in combination with stereotactic radiotherapy-induced tumour necrosis in patients with previously treated colorectal cancer" The 2013 SRS/SBRT Scientific Meeting hosted by the Radiosurgery Society, Carlsbad, California, Feb. 21-23, 2013, Abstract.

(56) References Cited

OTHER PUBLICATIONS

Mahadevan, A. et al. "Induction gemcitabine and stereotactic body radiotherapy for locally advanced nonmetastatic pancreas cancer" *Int. J. Radiation Oncol. Biol. Phys.*, 2011, 81(4):e615-e622.

Mahadevan, A. et al. "Stereotactic body radiotherapy and gemcitabine for locally advanced pancreatic cancer" *Int. J. Radiation Oncol. Biol. Phys.*, 2010, 78(3):735-742.

Schellenberg, D. et al. "Gemcitabine chemotherapy and single-fraction stereotactic body radiotherapy for locally advanced pancreatic cancer" *Int. J. Radiation Oncol. Biol. Phys.*, 2008, 72(3):678-686.

\* cited by examiner

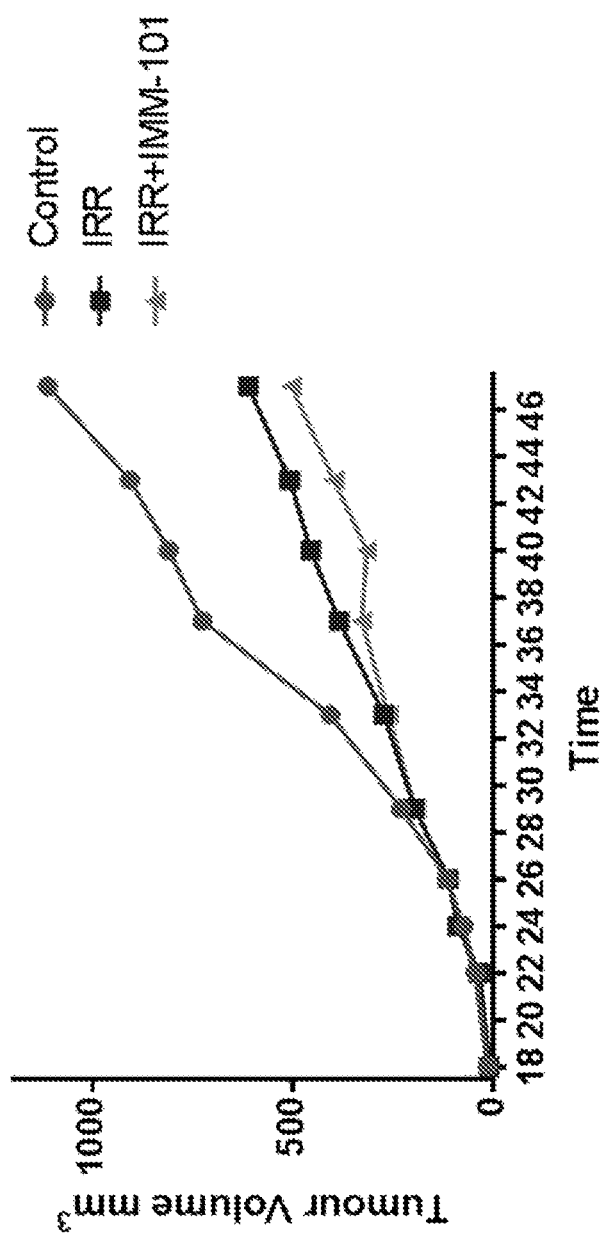

IMMUNOGENIC TREATMENT OF CANCER

CROSS REFERENCE TO RELATED APPLICATIONS

This application is a continuation of U.S. patent application Ser. No. 16/225,028, filed Dec. 19, 2018, now U.S. Pat. No. 11,318,193, which is a continuation of U.S. patent application Ser. No. 14/361,992, filed May 30, 2014, now abandoned, which is a U.S. National Stage application under 35 U.S.C. § 371 of International Application No. PCT/GB2012/052992, filed Dec. 3, 2012, which claims priority to Great Britain Application No. 1120779.2, filed Dec. 2, 2011, the disclosures of which are incorporated herein by reference in their entirety.

FIELD OF THE INVENTION

The present invention relates to the field of cancer therapy. In particular, the present invention relates to a method of treating the development of tumours or metastases in a subject and to an immunomodulator for use in such therapy, in combination with a procedure which results in localized tumour cell damage or immunological cell death.

BACKGROUND OF THE INVENTION

In recent years there has been a growing realization that immune responses play a central role in cancer biology by eliminating many tumours at a very early stage and keeping those that avoid total elimination in a state of equilibrium, sometimes for many years (Dunn et al, Annu Rev Immunol 2004; 22:329-360). The eventual escape from this equilibrium phase with clinical manifestation of the disease is associated with dysregulated immune responses, manifesting, for example, as chronic inflammation or immunesuppression. The strong and increasing evidence that the immune system is critically involved in the development, structural nature and progression of cancer has led to renewed interest in immunotherapeutic strategies for treatment of this class of diseases. To date, most attempts to develop such strategies have been based on the use of antigens derived from the patient's own tumour or from tumour cell lines and the transfer of ex-vivo expanded populations of tumour antigen-specific cytotoxic cells and antigen-presenting cells.

Cancer has been associated with inflammation since 1863, when Rudolf Virchow discovered leucocytes in neoplastic tissues and so made the first connection between inflammation and cancer (Balkwill et al, Lancet 2001; 357:539-545). Since then, chronic inflammation has been deemed to be a risk factor for cancer. These reports demonstrate that an inflammatory environment supports tumour development and is consistent with that observed at tumour sites. However, the relationship of cancer with inflammation is not limited to the onset of the disease due to chronic inflammation. Schwartsburd (Cancer and Metastasis reviews 2003; 22:95-102) proposed that chronic inflammation occurs due to tumour environment stress and that this generates a shield from the immune system. It has been recently demonstrated that the tumour microenvironment resembles an inflammation site, with significant support for tumour progression, through chemokines, cytokines, lymphocytes and macrophages which contribute to both the neovascularisation and vasal dilation for increased blood flow, the immunosuppression associated with the malignant disease, and the establishment of tumour metastasis. Furthermore, this inflammation-site tumour-generated microenvironment, apart from its significant role in protection from the immune system and promotion of cancer progression, has an adverse effect on the success of current cancer treatments. Indeed, it has been found that the inflammatory response in cancer can compromise the pharmacodynamics of chemotherapeutic agents (Slaviero et al, Lancet Oncol 2003; 4:224-32).

Moreover, metastatic cancer cells leave the tumour as microcolonies, containing lymphocytes and platelets as well as tumour cells. Inflammation continues to play a role at metastatic sites by creating a cytokine milieu conducive to tumour growth.

Immune homeostasis consists of a tightly regulated interplay of pro- and anti-inflammatory signals. For example, loss of the anti-inflammatory signals leads to chronic inflammation and proliferative signalling. Interestingly, cytokines that both promote and suppress proliferation of the tumour cells are produced at the tumour site. As in the case of cancer initiation, it is the imbalance between the effects of these various processes that results in tumour promotion.

It is believed that, to treat cancer, the most effective type of immune response is of a Type 1, which favours the induction of CD4+Th1 cellular responses, and of CD8+CTL responses. In the context of cancer vaccines, many immune stimulants are used, which promote the development of Th1 responses and are thought to inhibit the production of a Th2 response.

To date, a major barrier to attempts to develop effective immunotherapy for cancer has been an inability to break immunosuppression at the cancer site and restore normal networks of immune reactivity. The physiological approach of immunotherapy is to normalize the immune reactivity so that the endogenous tumour antigens would be again recognized and effective cytolytic responses would be developed against cells bearing these antigens.

Anti-cancer immune responses accompanying the action of chemo- and radiotherapy have been recently reviewed and show that such responses are critical to therapeutic success by eliminating residual cancer cells and maintaining micrometastases in a state of dormancy (Zitvogel et al, J Clin Invest 2008; 118:1991-2001). However, this reference makes it clear that there is no simple immunotherapeutic strategy available for consistently enhancing such immune responses.

There is evidence that therapeutic procedures that induce certain forms of immunogenic cancer cell death also lead to release of tumour antigens. There are three main types of cell death (Tesniere et al, Cell Death Differ 2008; 15:3-12): apoptosis (type 1), autophagy (type 2) and necrosis (type 3). Apoptosis, or programmed cell death, is a common and regular occurring phenomenon essential for tissue remodelling, especially in utero but also ex utero. It is characterized by DNA fragmentation in the nucleus and condensation of the cytoplasm to form rapoptotic bodies' which are engulfed and digested by phagocytic cells. In autophagy, cell organelles and cytoplasm are sequestered in vacuoles which are extruded from the cell. Although this provides a means of survival for cells in adverse nutritional conditions or other stressful situations, excess autophagy results in cell death. Necrosis is a 'cruder' process characterized by damage to intracellular organelles and cell swelling, resulting in rupture of the cell membrane and release of intracellular material.

It has widely been held that apoptosis is immunologically 'silent', as would be expected from its physiological role and by the finding that local inflammation is suppressed by the release of anti-inflammatory mediators. More recently it has been suggested that there are different forms of apoptosis and some are immunogenic (Zitvogel et al, Adv Immunol 2004; 84: 131-179). The relationship of autophagy to immunogenicity is poorly understood but necrosis certainly releases many antigens, although in progressive cancers, such necrosis might also enhance the chronic inflammation that favours tumour growth (Vakkila et al, Nat Rev Immunol 2004; 4: 641-648; Zeh et al, J Immunother 2005; 28:1-9). In this sense, a cancer resembles a chronically inflamed wound that does not heal (Dvorak. N Engl J Med 1986; 315:1650-1659).

Necrosis has been principally classified as immunogenic cell death. A limited number of studies indicate that procedures inducing immunogenic cell death release mediators and tumour antigens that are able to both induce immune responses, including activation of cytotoxic CD8+ T cells and NK cells and act as targets, including rendering antigens accessible to Dendritic Cells (DC), able in principle to create an in vivo DC vaccine.

It is more useful to categorize cell death into immunogenic and non-immunogenic forms, irrespective of the precise mechanism of such cell death. In a therapeutic setting with restoration of beneficial immune regulation, antigens released by immunogenic cell death would then be able to elicit effective anti-tumour immune responses, particularly if they are release in the presence of Danger-Associated (or Damage-Associated) Molecular Pattern (DAMP) (Jerome et al., N. Eng. J. Med. 2004; 350: 41141-2).

Efforts have been made in the art to provide combined ablative and chemotherapies for the treatment of tumours. WO2000064476 and US20050187207 disclose the use of an immunoadjuvant in combination with photodynamic therapy for the treatment of metastatic tumours. These documents disclose that the immunoadjuvant comprises mycobacterial cell wall skeletons and de-3-O-acylated lipid A and is administered by injection into the tumour. Castano et al (Nat Rev Cancers 2006; 6:535), Korbelik et al (J Photochem and Photobiol 1998; 44:151) and Korbelik et al (J Photochem and Photobiol, 2001; 73:403) also disclose the treatment of tumours using a combination of photodynamic therapy and the administration of mycobacterial cell wall extract as an immunoadjuvant. Mycobacterial cell walls contain compounds such as trehalose dimycolate and muramyl dipeptide which are known immunostimulators. The mycobacterial cell wall extracts used in the prior art combination therapies also elicit pro-inflammatory cytokines, reactive nitrogen species and recruit leukocytes which are associated with pathology including weight loss due to TNF-α mediated cachexia, with associated lipidemia, hypoglycaemia and peritonitis with ischemic and hemorrhagic lesions in the GI tract. The prior art combination therapies may therefore exacerbate the inflammatory response and have severe side-effects.

SUMMARY OF THE INVENTION

The present invention provides a safe, well-tolerated and effective method for treating cancer by employing techniques leading to immunogenic cell death which act synergistically with immunotherapy. The present invention provides a combination of an immunogenic cell death therapy applied to a tumour together with a specific type of immunotherapy. The inventors have found that the combination of both therapies is synergistic beyond simple additive effects of each therapy used individually.

In a first aspect, the invention provides an immunomodulator for use in the treatment and/or control of a neoplastic disease in a patient intended to undergo immunogenic cell death therapy simultaneously, separately or sequentially with administration of the immunomodulator.

In a second aspect, the invention is a method of treating, inhibiting or controlling the development of a tumour in a subject comprising undertaking immunogenic cell death therapy in a subject and the simultaneously, separate or sequential administration to the subject of an effective amount of an immunomodulator.

DESCRIPTION OF THE DRAWINGS

The invention is described with reference to the following drawing, in which:

FIG. 1 shows the results of a study on the effect of administering an immunomodulator (heat-killed *Mycobacterium obuense*; IMM-101) to an animal undergoing ablative irradiation treatment for cancer. The results show that the combination is synergistically better than treatment by irradiation alone.

DETAILED DESCRIPTION OF THE INVENTION

An immunomodulator, as defined according to the present invention, is a component which stimulates Type 1 response and down regulates Th2 responses and which restores the healthy balance of the immune system, through immunoregulation.

The present invention requires immunogenic cell death therapy. This therapy results in the induction of tumour immunogenic cell death, including apoptosis (type 1), autophagy (type 2) and necrosis (type 3), whereupon there is a release of tumour antigens that are able to both induce immune responses, including activation of cytotoxic CD8+ T cells and NK cells and to act as targets, including rendering antigens accessible to Dendritic Cells. The procedures which cause immunogenic cell death of the tumour, are highlighted below.

In the context of the present invention, "immunogenic tumour cell death therapy" refers to the ability to physically induce damage in a tumour or tumour cells, so that the cells release antigens which are utilised by the immune system to recognize and target the tumour. The term includes ablative therapies. The release of tumour antigens can be shown by observing an increase in, for example, recall responses and cytotoxic T cell responses.

The immunogenic cell death therapy may be carried out at sub-optimal levels, i.e. non-curative therapy such that it is not intended to fully remove or eradicate the tumour, but nevertheless results in some tumour cells or tissue becoming necrotic. The skilled person will appreciate the extent of therapy required in order to achieve this, depending on the technique used, age of the patient, status of the disease and particularly size and location of tumour or metastases.

Simultaneous administration, as defined herein, includes the administration of the immunomodulator and cell death therapy procedure within about 2 hours or about 1 hour or less of each other, even more preferably at the same time.

Separate administration, as defined herein, includes the administration of the immunomodulator and cell death therapy procedure more than several weeks, several days, about 12 hours, or about 8 hours, or about 6 hours or about 4 hours or about 2 hours apart.

Sequential administration, as defined herein, includes the administration of the immunomodulator and cell death therapy procedure in multiple aliquots and/or doses and/or on separate occasions. Preferably the immunomodulator is administered before and continued to be administered to the patient after the cell death therapy procedure occurs. More preferably, the immunomodulator is continued to be applied to the patient after treatment for regression of the tumour.

In one aspect of the present invention the immunomodulator comprises heat-killed *Mycobacterium*. Preferred mycobacterial species for use in the present invention include *M. vaccae, M. thermoresistibile, M. flavescens, M. duvalii, M. phlei, M. obuense, M. parafortuitum, M. sphagni, M. aichiense, M. rhodesiae, M. neoaurum, M. chubuense, M. tokaiense, M. komossense, M. aurum, M. w, M. tuberculosis, M. microti; M. africanum; M. kansasii, M. marinum; M. simiae; M. gastri; M. nonchromogenicum; M. terrae; M. triviale; M. gordonae; M. scrofulaceum; M. paraffinicum; M. intracellulare; M. avium; M. xenopi; M. ulcerans; M. diemhoferi, M. smegmatis; M. thamnopheos; M. flavescens; M. fortuitum; M. peregrinum; M. chelonei; M. paratuberculosis; M. leprae; M. lepraemurium* and combinations thereof.

Preferably, the heat-killed *Mycobacterium* is non-pathogenic. The non-pathogenic heat-killed *Mycobacterium* is selected from *M. vaccae, M. obuense, M. parafortuitum, M. aurum, M. w, M. phlei* and combinations thereof. More preferably the non-pathogenic heat-killed *Mycobacterium* is a rough variant. The amount of immunomodulator administered to the patient is sufficient to elicit a protective immune response in the patient such that the patient's immune system is able to mount an effective immune response to tumour cell antigens following tumour cell ablation, or immunogenic cell death. In certain embodiments of the invention, it is preferable that particular a dosage of immunomodulator be administered to a subject. Thus, in certain embodiments of the invention, there is provided a containment means comprising the effective amount of heat-killed *Mycobacterium* for use in the present invention, which typically may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. The effective amount of heat-killed *Mycobacterium* for use in the present invention may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. Most preferably the amount of heat-killed *Mycobacterium* for use in the present invention is from $10^7$ to $10^9$ cells or organisms. Typically, the composition according to the present invention may be administered at a dose of from $10^8$ to $10^9$ cells for human and animal use. Alternatively the dose is from 0.01 mg to 1 mg or 0.1 mg to 1 mg organisms presented as either a suspension or dry preparation.

*M. vaccae* has the ability to modulate immune responses. Its Type 1 adjuvant property is unaffected by heat-killing, whereas other mycobacteria, such as BCG, have little Type 1 adjuvant effect when dead. *M. vaccae* also downregulates pre-existing Th2 responses in a manner that appears to be independent of its ability to enhance Type-1 responses. This effect has now been attributed to induction of CD4+ CD45RB$^{low}$ regulatory T-cells that in an experimental model of pulmonary allergic inflammation can suppress allergic inflammation and airway hyper-reactivity when transferred to allergic recipients. *M. obuense* also shows immunomodulatory effects.

Unlike agents that target single cytokine mediators, *M. vaccae* has a wider effect through its ability to reduce several Th2 cytokines, including IL-4, IL-5 and IL-13, via immunoregulatory mechanisms including induction of regulatory T-cells that down-regulate Th2 via a mechanism involving IL-10 and Transforming growth factor (TGF)-β.

*M. vaccae* and *M. obuense* induce a complex immune response in the host. Treatment with these preparations will stimulate innate and type-1 immunity (Th1 and CD8+CTLs) akin to what has been observed with treatment with other mycobacterial preparations (for example live attenuated BCG and mycobacterial cell wall extracts). However, a significant additional benefit of treatment with *M. vaccae* and *M. obuense*, is the regulation of the immune response through the induction of regulatory cells (T-regulatory and DC with regulatory phenotype) which control and modulate prolonged and over-exuberant immune reactions (for example, following tumour ablation). Tight control of immune reactions through immunoregulation not only limits tissue pathology but also ensures a quick return to energy efficient steady state immune equilibrium.

The present invention may be used to treat, control or inhibit a neoplastic disease. Cancers that may be treated according to the invention include but are not limited to cells or neoplasms of the bladder, blood, bone, bone marrow, brain, breast, colon, esophagus, gastrointestines, gum, head, kidney, liver, lung, nasopharynx, neck, ovary, prostate, skin, stomach, testis, tongue, or uterus. In addition, the cancer may specifically be of the following histological type, though it is not limited to the following: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumour, malignant; bronchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma with squamous metaplasia; thymoma, malignant; ovarian stromal tumour, malignant; thecoma, malignant; granulosa cell tumour, malignant; androblastoma, malignant; Sertoli cell carcinoma; Leydig cell tumour, malignant; lipid cell tumour, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumour; Mullerian mixed tumour; nephroblastoma; hepatoblastoma; carcinosarcoma; mesenchymoma, malignant; Brenner tumour, malignant; phyllodes tumour, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumour of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumour; meningioma, malignant; neurofibrosarcoma; neurilemmoma, malignant; granular cell tumour, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Preferably, the neoplastic disease may be tumours associated with a cancer selected from prostate cancer, liver cancer, renal cancer, lung cancer, breast cancer, colorectal cancer, pancreatic cancer, brain cancer, hepatocellular cancer, lymphoma, leukaemia, gastric cancer, cervical cancer, ovarian cancer, thyroid cancer, melanoma, head and neck cancer, skin cancer and soft tissue sarcoma and/or other forms of carcinoma. The tumour may be metastatic or a malignant tumour.

Ablation-induced damage of the tumour is characterized for example by antigen leakage, cellular debris and release of mediators which give rise to a strong immune reaction. The further addition of an insult such as one delivered by the intratumoural administration of mycobacterial cell wall extract of the prior art further stimulates the immune system leading to additional inflammation and immune reactivity to shared and tumour antigens. Because of its nature, this response to the mycobacterial cell wall extract may proceed uncontrolled. Pre-treatment with heat-killed whole cell *M. vaccae* and *M. obuense* gives rise to more complex immunity including not only the development of innate immunity and type-1 immunity, but also immunoregulation which more efficiently restores appropriate immune functions.

The immunogenic cell death therapy is preferably carried out on metastatic cancer cells or tissue rather than the primary tumour. Metastatic cancer cells are those cancer cells that have spread from the primary tumours. Treatment is carried out with the aim of causing disruption to the tumours such that there is the release of tumour antigens which can then be recognised by the immune system. Accordingly, the treatment can be carried out at sub-lethal levels, sufficient to induce a minimal cell damage. The metastatic cancer cells or tissue may be present in an organ or site different to that of the primary tumour.

The metastatic cancer may be identified using techniques conventional in the art, including lab tests, x-rays, computed tomography (CT) scan, magnetic resonance imaging (MRI) scan and position emission tomography (PET) scan, or combinations thereof.

The treatment does not have to result in eradication, but can aim at disrupting a proportion of the cells or tissue, to trigger an immune response, e.g. the treatment can result in necrosis of the proportion of the metastatic cancer cells or tissue. In this regard, the techniques may be employed under sub-optimal conditions, requiring only to disrupt a proportion of the cells or tissue.

Before and/or after disruption of the tumour tissue, effective amounts of the immunomodulator, e.g. whole-cell *Mycobacterium*, may be administered in multiple (repeat) doses, for example two or more, three or more, four or more, five or more, ten or more, or twenty or more repeat doses, at intervals of about 2 weeks, or about 4 weeks or about 8 weeks.

Alternatively, the immunogenic cell death therapy may be performed simultaneously with the administration of the effective amounts of the immunomodulator (e.g. whole-cell *Mycobacterium*).

In a further embodiment the immunogenic cell death therapy may be performed after the administration of the effective amount of the immunomodulator (e.g. whole-cell *Mycobacterium*).

In a further embodiment immunogenic cell death therapy may be performed or administered after the administration of the effective amount of the immunomodulator (e.g. whole-cell *Mycobacterium*).

In a further embodiment the immunogenic cell death therapy is performed or administered before the administration of the effective amount of the *Mycobacterium*.

The immunomodulator may be administered to the patient via the parenteral, oral, sublingual, nasal or pulmonary route. In a preferred embodiment, the immunomodulator is administered via a parenteral route selected from subcutaneous, intradermal, subdermal, intraperitoneal, intravenous and intravesicular injection. More preferably, administration by the parenteral route does not comprise intratumoural injection of mycobacterial cell wall extract.

The immunogenic cell death therapy may comprise any means of physical denaturation or disruption of the tumour tissue including tumour ablation. Ablation may involve any minimally invasive technique designed to destroy malignant tissue with minimal damage to surrounding normal tissue. These techniques have received considerable interest in recent years because of their potential for decreased cost, lower morbidity, and utilization in an outpatient setting. Additionally, in contrast to surgical resection, tumour recurrences can be readily treated with these newer ablative therapies. In a preferred embodiment the ablative tumour disruptive therapy may be selected from microwave irradiation, radiofrequency ablation, targeted radiotherapy, embolisation, cryotherapy, ultrasound, high intensity focused ultrasound, cyberknife, hyperthermia, cryoablation, electrotome heating, hot water injection, alcohol injection, embolization, radiation exposure including Cesium-131 brachytherapy (internal radiation therapy) seeds, photodynamic therapy, laser beam irradiation and combinations thereof. However, the means of physical denaturation or disruption is not limited to these examples, and any means that can induce immunogenic cell death of tumour cells in a tumour tissue can be used. More preferably, two or more kinds of ablative tumour therapies may be suitably combined. The means of physical denaturation or disruption of the tumour tissue preferably results in necrosis or apoptosis of at least a portion of the tumour cells. The means of physical denaturation or disruption of the tumour tissue may cause sub-lethal damage to at least a portion of the tumour cells or tissue.

In a particularly preferred embodiment, the means of immunogenic tumour cell death therapy comprises irradiation, including ionizing radiation such as gamma rays, UV-C irradiation, targeted radiation, and the like.

In another embodiment, the therapy comprises irradiation, including ionizing radiation such as gamma rays, UV-C irradiation, targeted radiation, and the like, combined with administration of the immunomodulator, wherein the dose of radiation is fractionated. Suitable irradiation dosage regimes include a single full dose or about 3 fractions each comprising about 40% or more of the full dose, or about 5 fractions each comprising about 30% or more of the full dose, or doses and fractions as known to those skilled in the art.

In another particularly preferred embodiment, the means of immunogenic cell death therapy comprises irradiation, including ionizing radiation such as gamma rays, UV-C irradiation, targeted radiation, and the like, combined with administration of the immunomodulator, resulting in an abscopal effect.

Ionizing radiation can reduce tumour growth outside the field of radiation, known as the abscopal effect, from the Latin "ab scopus", "away from the target". Although it has been reported in multiple malignancies, the abscopal effect remains a rare and poorly understood event. Their rare occurrence reflects the fact that, by itself, standard radiotherapy is inadequate at subverting the existing immunosuppression characteristic of the microenvironment of an established tumour.

An abscopal effect is defined as a measurable response in any of the measurable lesions outside the radiation field, as assessed by PET-CT.

Specifically, radiation therapy causes upregulation or release of signals within a tumour that invoke Dendritic Cell (DC) migration to the tumour, uptake of tumour antigens, and maturation. These antigen-loaded DC migrate to regional lymph nodes and activate tumour antigen—specific T cells capable of tumour destruction. Finally, radiation therapy may eliminate regulatory immune cell populations that would otherwise hinder the development of effective antitumor T-cell responses (Morse et al, commentary; Oncology: August 2008. Vol. 22 No. 9).

In another preferred embodiment, the means of immunogenic cell death therapy comprises irradiation, including ionizing radiation such as gamma rays, UV-C irradiation, targeted radiation, and the like, combined with administration of the immunomodulator, resulting in an abscopal effect, as demonstrated by regression of local tumours and/or distant metastases.

In another particularly preferred embodiment, the invention provides an immunomodulator for use in the treatment of a neoplastic disease in a patient intended to undergo immunogenic cell death therapy by cyberknife, simultaneously, separately or sequentially with administration of the immunomodulator, optionally for the treatment of colorectal cancer or metastases derived therefrom.

A suitable dosage schedule according to the present invention includes administration of the immunomodulator at 2 weeks prior to and on the day of said ablative or immunogenic tumour cell death therapy, followed by further doses of said immunomodulator 2 weeks and 4 weeks later. Further doses of immunomodulator may be administered at weekly or fortnightly intervals such as at 8 weeks, 10 weeks and 12 weeks. Preferably the immunomodulator is continued to be administered at week 16 after ablative or immunogenic cell death therapy and repeated every 4 weeks thereafter for up to 12 months following the first dose given.

In some cases the immunogenic cell death therapies may require open surgical exposure of the tumour but most can be performed with minimal risk laparoscopically or percutaneously. In addition to cost savings, the percutaneous route has the potential for performance under conscious sedation, thus further reducing potential morbidity.

Radiofrequency ablation (RFA) and cryoablation is used primarily for liver tumours, is an invasive procedure requiring the insertion of a probe and is not without risk. In addition to direct tumour destruction, there is strong evidence that anti-tumour immune responses are generated by the procedure. (Napoletano et al Int J Oncol 2008; 32:481-490).

RFA, laser and microwave ablation all produce tissue death via hyperthermic injury. RFA produces thermal injury through the use of alternating electric current in the radiofrequency range (460-500 kHz). Subsequent ionic agitation in the surrounding tissue causes frictional heat, which then spreads outward from the electrode via conduction. Suitable RF devices commercially marketed in the United States may be obtained from RITA Medical Systems Inc., Mountain View, Calif., and Radiotherapeutics, Mountain View, Calif. These devices consist of a needle with a movable hub that deploys a variable number of curved electrodes into the adjacent tissue in a radial manner. The configurations of the multiple electrodes are designed to produce large spherical thermal injuries. A further device (Radionics, Burlington, Mass.) consists of a straight, internally cooled needle electrode. The internal cooling is designed to prevent charring of the adjacent tissues and thus a larger thermal injury. Other suitable apparatus include the computer-assisted radiofrequency generator (Elektrotom 106 HF, Berchtold, Tuttlingen, Germany) optionally emplying water-cooled treatment probes (Cool-Tip, ValleyLab, Boulder, Colo.). RFA needles, such as those with an active tip of 8 mm (SMK-15; Cotop, Amsterdam, the Netherlands) may be used in combination with an RF lesion generator system (Model RFG-3B, Radionics, Burlington, Mass.). Treatment preferably results in a tip temperature of 75-80° C. or even above 100° C. in certain tumours or metastases. If the temperature at the tip is below 50° C., another ablation in the same location is preferably performed.

The leakage of tumour antigens following tumour damage by laser-induced thermotherapy is supported by the observation that following treatment there is an enhancement of cytotoxic T cell responses. In a study of 11 patients with hepatic metastases of colorectal cancer treatment significantly increased the cytolytic activity of CD3+, CD4+ and CD8+ T cells against an allogenic tumour cell line (Vogl et al, Cancer Immunol Immunother 2009; 58:1557-1563). SABR has also been shown to create an environment leading to enhanced anti-tumour immune responses by inducing tumour antigen leakage in the presence of DAMPs such as heat shock proteins (Finkelstein et al. Clin and Dev Immunol; vol 2011: ID 439752). We propose that these effects can be induced using low-dose irradiation delivery in conjunction with an immunotherapeutic agent which will establish a self-sustaining long-term immunological response to the tumour and promote anti-tumour immunity.

Significant complications are rare with any of the RFA techniques, although most series report a few patients with minor complications requiring no specific treatment. Among the reported complications, the most common is pain, although this is typically of short duration. Other reported complications include fever, intraperitoneal and intrahepatic hemorrhage, hemobilia, hemothorax, diaphragmatic injury, pleural effusion, cholecystitis, elevated transaminase levels, and needle tract seeding.

Stereotactic ablative radiotherapy (SABR) may be used in the present invention as a form of physical tumour disruption to induce immunogenic tumour cell death. SABR is a form of radiosurgery for tumours in the torso. SABR, which is also sometimes referred to as stereotactic body radiotherapy or SBRT, has shown promise for the treatment of both inoperable and operable stage 1 non-small cell lung cancer (NSCLC). The effective radiosurgical dose was in the range of 15-20 Gy. Systems and methods for performing stereotactic radiosurgery are known in the art and are disclosed, e.g., in U.S. Pat. No. 5,207,223, issued to Adler on May 4, 1993, and U.S. Pat. No. 5,458,125, issued Oct. 17, 1995 to Schweikard, which are incorporated by reference in their entirety herein.

Microwave ablation may be used as an alternative means of producing thermal coagulation of tissue involves the use of microwaves to induce an ultra-high-speed (2450 MHz) alternating electric field, resulting in the rotation of water molecules. As with RFA microwave ablation involves placement of a needle electrode directly into the target tumour. Suitable apparatus include the Acculis Microwave Tissue Ablation (MTA) system (From Microsulis Medical) which operates at 2.45 GHz and is a very powerful apparatus when compared to Radio Frequency Ablation (RFA) devices and low power 915 MHz microwave systems. The system comes with the choice of a range of needle-like applicators to maximise the types of procedure for which it can be used: open, laparoscopic and percutaneous. Microwave energy emits from the tip of the applicator and is absorbed by the surrounding tissue. The depth of absorption depends on microwave frequency and power. This is controlled through the Sulis VpMTA generator. At 2.45 GHz, the energy will penetrate 2 cm into the tissue. This is the active microwave heating zone. Inside the active microwave heating zone the microwaves rotate the water molecules causing them to heat rapidly. Heat from the active microwave heating zone then conducts outwards creating a secondary thermal conduction heating zone. This completes the treatment. The coagulation zone is largely spherical, with a slight elongation in the direction of the shaft of the applicator. By selecting power and time the user can control both the size and rate of development of the coagulation zone. The active microwave heating creates visible steam formation within the target zone and this can be monitored in real time by intra-operative ultrasound or CT imaging giving real time control.

Reported complications of microwave ablation are similar to those reported for RFA and are typically mild, including pain, fever, liver enzyme elevation, ascites/pleural effusion, diaphragm injury, and needle track seeding.

In an alternative embodiment, laser ablation may be used. This technique uses a neodymium yttrium aluminium garnet (Nd-YAG) laser to deliver high-energy light to the target lesion. The light subsequently scatters within the tissue, converting to heat. Optical fibres are deposited into the tumour through a percutaneously placed needle. Multiple fibres can be inserted into the tumour at regularly spaced intervals to enlarge the area of necrosis. Treatment times vary but may exceed 1 hour for a large ablation. Another alternative is focal laser ablation (FLA) which is defined as the thermal destruction of tissue by laser. FLA action is based on a photothermal effect; the thermal action results from the absorption of radiant energy by tissue receptive chromophores inducing heat energy in a very short time (few seconds). This increased temperature may cause irreversible damages and remotely in vivo destruction. The thermal effect depends on the amount of heat energy delivered but also on the depth of light distribution. Consequently, the deep tissue damage is dependent on the wavelength of the laser in action. Due to weak absorption by water or hemoglobin, wavelengths between 590 and 1064 nm are classically used to obtain a deeper tissue penetration. The extension of thermal tissue damage depends on both temperature and heating duration. Cell viability is in relation with thermostability of several critical proteins. Irreversible protein denaturation may occur around 60° C., while over 60° C., coagulation is quasi-instantaneous, between 42 and 60° C., the preferred range for use in this invention, a thermal damage is obtained with longer heating periods. The area submitted to supraphysiological hyperthermia less than 60° C. will develop coagulative necrosis in 24 to 72 h after treatment.

Cryoablation may be used as an alternative to causing thermal injury to tissue through heating. Cryoablation destroys tissue by delivering subfreezing temperatures via probes through which a cryogen is circulated. Cellular death results from direct freezing, denaturation of cellular proteins, cell membrane rupture, cell dehydration, and ischemic hypoxia. Although freezing potentially produces the largest ablations of all the thermal techniques, the procedure in its most commonly practiced form requires general anaesthesia and laparotomy for probe placement. Cryoablation may be performed at a temperature of about minus 40 degrees Celsius, or about minus 60 degrees Celsius, or may be carried out using liquid nitrogen (−170 degrees Celsius) and applied by a contact method with the Cryobar equipment (Tori). During cryoablation the interface of the frozen/unfrozen liver can be assessed easily with intra-operative ultrasound by the appearance of an echogenic edge with posterior acoustic shadowing, an advantage of cryoablation over RFA In certain embodiments therefore, cryoablation is a preferred method of inducing immunogenic tumour cell death, compared to thermal methods.

The complication rate for cryoablation may be higher than that for RFA, although cryoablation may not be as limited by lesion size. In addition, there exists evidence that lung inflammation may be a complication unique to cryoablation and may be related to the thawing phase of the ablated tissue.

In an alternative embodiment, ethanol ablation may be used as the ablative therapy. Percutaneous ethanol injection (PEI) is relatively simple to perform, and is the least expensive, requiring minimal equipment. PEI is performed by the injection of absolute alcohol through a needle placed percutaneously directly into a tumour. The necrosis produced by ethanol injection results from cellular dehydration and tissue ischemia from vascular thrombosis. Ethanol ablation may also be considered for recurrent or partially treated disease previously managed with an alternative minimally invasive technique. Contraindications to treatment include those mentioned above for RFA in addition to thrombosis of the main portal vein. Patients with obstructive jaundice may also be at increased risk for complications such as bile peritonitis. As with the aforementioned techniques, the complete ablation rate with ethanol is higher for small tumours.

Embolization is an established technique for the treatment of hepatic tumours. Embolization is an endovascular technique, (performed from within the blood vessels) to block vessels of the tumour. Embolization is performed using catheters and angiographic techniques. For the embolization procedure, a very tiny catheter is threaded from the groin directly into the tumour vessels around the brain, head and neck, or spine, for example. Under X-ray guidance, material is injected through the catheter to permanently block and close off the vessels of the tumour. Materials used include particles or small platinum coils. The selection of embolic agent is directed by a balance between risk and efficacy. Smaller particles (45-150 microns) and liquid embolic agents (bucrylate, ethanol, ethylenevinylalcohol) penetrate tumour better and achieve a higher degree of necrosis. The operator's selection of embolic agent is directed by a balance between risk and efficacy. The critical size of microparticles is generally considered to be above 150 microns. In one study, populations of CD4+ T cells specific for epitopes of the tumour antigen α-fetoprotein were significantly expanded during and after embolization (Ayaru et al. J Immunol. 2007, 178:1914-1922). These T cells produced Th1 cytokines (IFN-γ and TNF-α) but not the Th2 cytokine IL-5 and the authors concluded that these results provided a rationale for combining embolization and immunotherapy. In another study (Zerbini et al Cancer Res 2006; 66:1139-1146), increased numbers of Th2 cells were demonstrated in patients one month after embolization, and the cells had increased expression of markers of cytotoxic activity. These T cells did not, however, prevent relapse of the disease and one patient developed a new nodule, the antigens of which were not recognized by the T cells, indicating immune escape. Thus additional immunotherapeutic strategies to maintain immune recognition are required.

In a yet further embodiment, photodynamic therapy may be used as the ablative therapy. Photodynamic therapy involves administering to a subject an effective amount of a photosensitizer and irradiating said subject with light absorbed by said photosensitizer. The effective amount of a photosensitizer may be in the range of 0.05 to 10 mg/kg, or 0.05 to 1 mg/kg, or 1 to 10 mg/kg. In the first step of PDT for cancer treatment, a photosensitizing agent is injected into the bloodstream. The agent is absorbed by cells all over the body but stays in cancer cells longer than it does in normal cells. Approximately 24 to 72 hours after injection, when most of the agent has left normal cells but remains in cancer cells, the tumour is exposed to light. The photosensitizer in the tumor absorbs the light and produces an active form of oxygen that destroys nearby cancer cells. In addition to directly killing cancer cells, PDT appears to shrink or destroy tumours in two other ways. The photosensitizer can damage blood vessels in the tumour, thereby preventing the cancer from receiving necessary nutrients. As required in this invention, PDT also activates the immune system to attack the tumour cells. The light used for PDT can come from a laser or other sources. Laser light can be directed through fiber optic cables (thin fibers that transmit light) to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumours, such as skin cancer.

The photosensitizer may be administered intravenously or intratumourally and the irradiation is preferably localized to the tumours. Suitable photosensitizers include benzoporphyrin derivative (BPD), e.g. BPD-MA, EA6, or B3 or a green porphyrin. Such photosensitizers may be formulated in a liposomal formulation.

The patient whom is to undergo immunogenic tumour cell death or ablative tumour disruption therapy according to the present invention may do so simultaneously, separately or sequentially with administration of the immunomodulator. Preferably the immunomodulator is administered to the patient prior to the physical tumour disruption therapy of the tumour tissue. More specifically, the immunomodulator may be administered to the patient between about 4 weeks and 1 week prior to the tumour disruption therapy. Preferably, the immunomodulator may be administered as one or more aliquots each containing an effective amount of the immunomodulator which may be administered at one or more time intervals between 4 weeks and 1 week prior to the tumour disruption therapy and/or the immunomodulator may be applied after the therapy. Even more preferably, the immunomodulator may be administered as one or more aliquots each containing an effective amount of the immunomodulator which may be administered at one or more time intervals between 4 weeks and 1 week after the tumour disruption therapy and/or the immunomodulator may applied after the therapy, and repeated on at least about 2, 4, 6, 8, 10, 12, 15, 20 or more occasions before or after the therapy.

In one embodiment of the present invention, the immunomodulator may be in the form of a medicament administered to the patient in a dosage form and/or in a schedule as set out in the examples.

In an aspect of the invention, the effective amount of the immunomodulator may be administered as a single dose. Alternatively, the effective amount of the immunomodulator may be administered in multiple (repeat) doses, for example two or more, three or more, four or more, five or more, ten or more, or twenty or more repeat doses. Preferably, the immunomodulator is administered between about 4 weeks and 1 day prior to tumour disruption therapy of the tumour tissue, more preferably between about 4 weeks and 1 week, or about between 3 weeks and 1 week, or about between 3 weeks and 2 weeks. Administration may be presented in single or multiple doses.

A container according to the invention in certain instances, may be a vial, an ampoule, a syringe, capsule, tablet or a tube. In some cases, the mycobacteria may be lyophilized and formulated for resuspension prior to administration. However, in other cases, the mycobacteria are suspended in a volume of a pharmaceutically acceptable liquid. In some of the most preferred embodiments there is provided a container comprising a single unit dose of mycobacteria suspended in pharmaceutically acceptable carrier wherein the unit dose comprises about $1 \times 10^6$ to about $1 \times 10^{10}$ CFU of mycobacteria. In some very specific embodiments the liquid comprising suspended mycobacteria is provided in a volume of between about 0.1 ml and 10 ml, about 0.3 ml and 2 ml or about 0.5 ml and 2 ml. It will further be understood that in certain instances a composition comprising mycobacteria in a containment means is frozen (i.e. maintained at less than about zero degrees Celsius). The foregoing compositions provide ideal units for immunotherapeutic applications described herein.

Embodiments discussed in the context of a methods and/or composition of the invention may be employed with respect to any other method or composition described herein. Thus, an embodiment pertaining to one method or composition may be applied to other methods and compositions of the invention as well.

In some cases heat-killed mycobacteria is administered to specific sites on or in a subject. For example, the mycobacterial compositions according to the invention, such as those comprising *M. obuense* in particular, may be administered adjacent to tumours or adjacent to lymph nodes, such as those that drain tissue surrounding a tumour. Thus, in certain instances sites administration of mycobacterial composition may be near the posterior cervical, tonsillar, axillary, inguinal, anterior cervical, sub-mandibular, sub mental or superclavicular lymph nodes. Such sites of administration may be on the right side, on the left side, or on both sides of the body. In certain very specific embodiments, mycobacterial compositions are delivered close to the axillary, cervical and/or inguinal lymph nodes. For example, a dosage of the mycobacteria may distribute into tissues adjacent to the right and left axillary lymph node and the right and left inguinal lymph nodes.

In a very specific embodiment a dosage of mycobacteria is administered to a subject by intradermal injection wherein the dosage is distributed to the axillary and inguinal on both sides of the body and wherein there are two injections (i.e. two wheals) at each site.

In some further embodiments of the invention, methods of the invention involve the administration of 2, 3, 4, 5, 6, 7, 8, 9, 10 or more doses of mycobacteria separated by a period of one day or more. In certain preferred embodiments such separate doses will be separated by several days, one week, two weeks, one month or more. For example, methods according to the invention may comprise administering 1 to 5 doses of mycobacteria over a period of three weeks or more. In yet further embodiments, methods of the invention comprise administering 1 to 5, 1 to 4, 1 to 3, 1 to 2 or 2 doses of mycobacteria over a period of about three weeks. Each dose administered may be the same or different dosage relative to a previous or subsequent dose administration. For example, in certain cases, it is preferred that a dosage of mycobacteria is lower than any dosage that was previously administered. Thus, in some specific cases, a dose of heat-killed mycobacteria will be administered at about half of the dosage that was administered in any previous treatment. Such methods may be preferred in certain instances where the subject's immune response to the mycobacteria is greater during subsequent therapies. Thus in certain cases, the immunomodulator may be administered a minimal number of times for example, in less than 10, 9, 8, 7, 6, 5, 4, 3 or fewer separate dosage administrations. In some cases the mycobacterial composition is administered twice. Alternatively, the immunomodulator may be administered for the length of time the cancer or tumour(s) is present in a patient or until such time the cancer has regressed or stabilized. The immunomodulator may also be continued to be administered to the patients once the cancer or tumour has regressed or stabilised.

Mycobacterial compositions according to the invention will comprise an effective amount of mycobacteria typically dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains mycobacteria will be known to those of skill in the art in light of the present disclosure, as exemplified by Remington's Pharmaceutical Sciences, 18th Ed. Mack Printing Company, 1990, Moreover, for animal (e.g., human) administration, it will be understood that preparations should meet sterility, pyrogenicity, general safety and purity standards. A specific example of a pharmacologically acceptable carrier as described herein is borate buffer or sterile saline solution (0.9% NaCl).

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavouring agents, dyes, such like materials and combinations thereof, as would be known to one of ordinary skill in the art (see, for example, Remington's Pharmaceutical Sciences, 18th Ed. Mack Printing Company, 1990, pp. 1289-1329).

In a preferred embodiment, the immunomodulator is administered via a parenteral route selected from subcutaneous, intradermal, subdermal, intraperitoneal, intravenous and intravesicular injection. Intradermal injection enables delivery of an entire proportion of the mycobacterial composition to a layer of the dermis that is accessible to immune surveillance and thus capable of electing an anti cancer immune response and promoting immune cell proliferation at local lymph nodes.

Though in highly preferred embodiments of the invention mycobacterial compositions are administered by direct intradermal injection, it is also contemplated that other methods of administration may be used in some case. Thus in certain instances heat-killed mycobacteria of the present invention can be administered by injection, infusion, continuous infusion, intravenously, intradermally, intraarterially, intraperitoneally, intralesionally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, intracranially, intraarticularly, intraprostaticaly, intrapleurally, intratracheally, intranasally, topically, locally, inhalation (e.g. aerosol inhalation), via a catheter, via a lavage, or by other method or any combination of the forgoing as would be known to one of ordinary skill in the art (see, for example, Remington's Pharmaceutical Sciences, 18th Ed. Mack Printing Company, 1990). More preferably, administration by the parenteral route does not comprise intratumoural injection of mycobacterial cell wall extract.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and immunology or related fields are intended to be within the scope of the following claims.

The invention is further described with reference to the following non-limiting Examples.

Example 1

To investigate the invention, we conducted a study in female Balb/c mice injected subcutaneously with an inoculum of Renca tumour cells and treated with irradiation therapy in combination with IMM-101 (*Mycobacterium obuense*, rough strain, heat-killed).

Briefly, adult mice were maintained under SPF conditions at controlled temperature (23±2° C.), Humidity (45±10%) and photoperiod (12 hr light/12 hr dark). They were provided with water and food at libitum. Mice were individually tagged for identity. At day 0, mice received subcutaneously an inoculum of $10^5$ Renca tumour cell in a 0.2 ml volume of RPMI 1640 medium in their right flank. Tumour establishment and growth was monitored daily. Once tumours became palpable (100-200 mm³ on day 25) mice were randomised and divided into three groups. Group 1 was left untreated. Group 2 and 3 received the following treatments: Group 2) two cycles of one irradiation of the tumour at 2Gy/day every two days for a total of three irradiations/cycle (total irradiation dose 12Gy, schedule [Q2D×3]×2 starting on day 25 and continuing on day 28, 30, 32, 35 and 37); Group 3) two cycles of irradiation as described above in synergy with IMM-101 (0.1 mg) injected subcutaneously about every two days, starting on day 25 and repeated on day 28, 30, 32, 35, 37, 39, 42 etc.

Animals were monitored daily and length and width of tumour measured twice a week with calipers to estimate tumour volume (½×length×width²). Individual body weight and tumour volume were recorded for each mouse. Data was graphed to follow changes in tumour volume over time in the three treatment groups (FIG. 1).

We found that compared to control untreated animals, mice receiving irradiation and IMM-101 showed a significant reduction in tumour volume (Anova, Dunne's comparison). This provides evidence that said combination treatment provides an improved therapy and improved survival outcome.

Example 2

An investigative study of a preparation of heat-killed whole cell *M. obuense* (IMM-101) in combination with radiation-induced immunogenic tumour necrosis in patients with previously treated colorectal cancer was conducted in patients according to the protocol described in Table 1. Patients were subjected to a dose of *M. obuense* IMM-101 on the same day as establishment of the baseline and insertion of the fudicial seeds required for correct focusing of cyberknife energy; subsequent SBRT using cyberknife technology to induce tumour necrosis was administered at day 14, together with a further dose of *M. obuense* (IMM-101). The patients received a further dose of *M. obuense* (IMM-101) on day 28 and then continued to receive *M. obuense* (IMM-101) doses at fortnightly intervals between week 8 and 12, inclusively, whereupon the dose frequency was reduced to monthly throughout the remaining period of the year-long study. Patients were then assessed for tumour regression and disease stabilisation at week 12 and every twelve weeks thereafter. The results show tumour regression after week 12 and then a prevalence of disease stabilisation at week 24 following continued administration of *M. obuense* (IMM-101) after the initial application of the cyberknife.

TABLE 1

| DAY | | | | | | WEEK | | | | | | | | | | |
|---|---|---|---|---|---|---|---|---|---|---|---|---|---|---|---|---|
| Screening (28 days max.) | 0§ | 7 | 14 | 21 | 28 | 5 6 7 | 8 | 9 | 10 | 11 | 13 14 12 15 | | 16 | 17 18 19 | 20 | 21 22 23 |
| * | ↑ * | * | ↑ * | ↑ * | ↑ * | ↑ * | ↑ * | | | | ↑ * | | ↑ * | ↑ * | | * |
| Consent Screening & Baseline CT | Baseline Fiducial Seed(s) | SBRT Planning | SBRT | | | | | | | | CT Scan Assessment of Disease Stabilisation | | Repeat CT Scan Confirm Stabilisation or Response | | | |

| WEEK | | | | | | | | | | | | | | |
|---|---|---|---|---|---|---|---|---|---|---|---|---|---|---|
| 24 | 25 26 27 | 28 | 29 30 31 | 33 34 32 35 | 36 | 37 38 39 | 40 | 41 42 43 | 44 | 45 46 47 | 48 | 49 50 51 | 52 |
| ↑ * | ↑ * | ↑ * | ↑ * | ↑ * | | ↑ * | ↑ * | ↑ * | | ↑ * | | | * |
| CT Scan Assessment of Disease Stabilisation | Repeat CT Scan Confirm Stabilisation or Response | | CT Scan Assessment of Disease Stabilisation | Repeat CT Scan Confirm Stabilisation or Response | | | | CT Scan Assessment of Disease Stabilisation | | Repeat CT Scan Confirm Stabilisation or Response | | | |

↑ = IMM-101 administration
* = Study Visit
Consent = The patient will be consented before any study related procedures are undertaken
Baseline CT = This will be used to identify an appropriate target metastasis
§ = Day 0 should be as soon as possible and no later than 17 days after eligibility is confirmed
SBRT = Necrosis will be induced using CyberKnife technology
Repeat CT = Repeat only if evidence of the disease stabilisation or response was documented in the previous CT scan

REFERENCES

Ayaru L, Pereira S P, Alisa A, et al. Unmasking of alpha-fetoprotein-specific CD4(+) T cell responses in hepatocellular carcinoma patients undergoing embolization. J Immunol. 2007; 178: 1914-1922.

den Brok M H, Sutmuller R P, Nierkens S, et al. Efficient loading of dendritic cells following cryo and radiofrequency ablation in combination with immune modulation induces anti-tumour immunity. Br J Cancer. 2006a; 95:896-905.

den Brok M H, Sutmuller R P, Nierkens S, et al. Synergy between in situ cryoablation and TLR9 stimulation results in a highly effective in vivo dendritic cell vaccine. Cancer Res 2006b; 66:7285-7292.

Dunn G P, Old L J, Schreiber R D. The three Es of cancer immunoediting. Annu Rev Immunol 2004; 22:329-360.

Dvorak H F. Tumors: wounds that do not heal. Similarities between tumor stroma generation and wound healing. N Engl J Med 1986; 315:1650-1659.

Finkelstein et al. The Confluence of Stereotactic Ablative Radiotherapy and Tumor Immunology. Clin and Dev Immunol: vol 2011: ID 439752.

Morse et al, An Odd But Synergistic Couple: Immunotherapy Combined With Radiotherapy; Oncology: August 2008. Vol. 22 No. 9).

Napoletano C, Taurino F, Biffoni M, et al. RFA strongly modulates the immune system and anti-tumor immune responses in metastatic liver patients. Int J Oncol 2008; 32:481-490.

Tesniere A, Panaretakis T, Kepp O, et al. Molecular characteristics of immunogenic cancer cell death. Cell Death Differ 2008; 15:3-12.

Vakkila J, Lotze M T. Inflammation and necrosis promote tumour growth. Nat Rev Immunol 2004; 4: 641-648.

Vogl T J, Wissniowski T T, Naguib N N, et al. Activation of tumor-specific T lymphocytes after laser-induced thermotherapy in patients with colorectal liver metastases. Cancer Immunol Immunother 2009; 58:1557-1563.

Zerbini A, Pilli M, Penna A, et al. Radiofrequency thermal ablation of hepatocellular carcinoma liver nodules can activate and enhance tumor-specific T-cell responses. Cancer Res 2006; 66:1139-1146.

Zeh H J, Lotze M T. Addicted to death: invasive cancer and the immune response to unscheduled cell death. J Immunother 2005; 28:1-9.

Zitvogel L, Casares N, Pequignot M O, et al. Immune response against dying tumor cells. Adv Immunol 2004; 84: 131-179.

Zitvogel L, Apetoh L, Ghiringhelli F, et al. The anticancer immune response: indispensable for therapeutic success? J Clin Invest 2008; 118:1991-2001.

We claim:

1. A method for treating a solid tumour in a human patient, the method comprising:
   applying an ablative tumour disruption therapy to the solid tumour to induce damage to the solid tumour or one or more cells of the solid tumour and release of tumour antigens, wherein the ablative tumour disruption therapy is targeted radiotherapy of the solid tumour, and wherein targeted radiotherapy of the solid tumour comprises a dose of radiation that is fractionated; and
   simultaneously, separately, or sequentially with the induction of damage to the solid tumour or one or more cells of the solid tumour, intradermally administering to the human patient an effective amount of an immunomodulator composition consisting of non-pathogenic heat-killed whole cell *Mycobacterium obuense*, wherein 0.01 mg to 1 mg of the non-pathogenic heat-killed whole cell *Mycobacterium obuense* is intradermally administered per dose, wherein the immunomodulator composition is intradermally administered in multiple doses and is intradermally administered prior to and after the ablative tumour disruption therapy, wherein the solid tumour is thereby regressed or stabilized.

2. The method of claim 1, wherein the targeted radiotherapy is stereotactic ablative radiotherapy.

3. The method of claim 1, wherein the intradermal administration of the immunomodulator composition occurs in the range of between 4 weeks and 1 week prior to the ablative tumour disruption therapy and is continued after the ablative tumour disruption therapy.

4. The method of claim 1, wherein the dose of radiation is applied in 3 to 5 fractions.

5. The method of claim 1, wherein the solid tumour is selected from the group consisting of prostate cancer, liver cancer, renal cancer, lung cancer, breast cancer, colorectal cancer, pancreatic cancer, brain cancer, gastric cancer, cervical cancer, ovarian cancer, thyroid cancer, head and neck cancer, and sarcoma.

6. The method of claim 1, wherein the solid tumour is metastatic.

7. The method of claim 1, wherein the effective amount of the immunomodulator composition comprises in the range of $10^3$ to $10^{11}$ cells of the non-pathogenic heat-killed whole cell *Mycobacterium obuense* per dose.

8. A method for treating solid metastatic cancer in a human patient, the method comprising:
   applying an ablative disruption therapy to solid metastatic cancer tissue at a site different to that of a solid primary tumour, wherein the ablative disruption therapy induces damage to the solid metastatic cancer tissue and release of tumour antigens, wherein the ablative disruption therapy is targeted radiotherapy, and wherein the targeted radiotherapy comprises a dose of radiation that is fractionated; and
   simultaneously, separately, or sequentially with the ablative disruption therapy, intradermally administering to the human patient an effective amount of an immunomodulator composition consisting of non-pathogenic heat-killed whole cell *Mycobacterium obuense*, wherein 0.01 mg to 1 mg of the non-pathogenic heat-killed whole cell *Mycobacterium obuense* is intradermally administered per dose, wherein the immunomodulator composition is intradermally administered in multiple doses and is intradermally administered prior to and after the ablative disruption therapy, and wherein the solid primary tumour and/or the solid metastatic cancer tissue is thereby regressed or stabilized.

9. The method of claim 8, wherein the solid metastatic cancer is selected from the group consisting of prostate cancer, liver cancer, renal cancer, lung cancer, breast cancer, colorectal cancer, pancreatic cancer, brain cancer, gastric cancer, cervical cancer, ovarian cancer, thyroid cancer, head and neck cancer, and sarcoma.

10. The method of claim 1, wherein the solid tumour is thereby regressed, and wherein said method further comprises continuing to intradermally administer the immunomodulator composition after the regression of the solid tumour.

11. The method of claim 8, wherein the solid primary tumour and/or solid metastatic cancer tissue is thereby regressed, and wherein said method further comprises continuing to intradermally administer the immunomodulator composition after the regression of the solid primary tumour and/or the solid metastatic cancer tissue.

12. The method of claim 1, wherein the solid tumour is a primary tumour.

13. The method of claim 1, wherein the solid tumour is adenocarcinoma.

14. The method of claim 8, wherein the solid metastatic cancer is adenocarcinoma.

* * * * *